US012527689B2

(12) United States Patent
Grüebler et al.

(10) Patent No.: US 12,527,689 B2
(45) Date of Patent: Jan. 20, 2026

(54) EXTENDIBLE IMPLEMENT FROM WITHIN A STIFFENING SLEEVE AND TOOL BODY END

(71) Applicant: Alcon Inc., Fribourg (CH)

(72) Inventors: Reto Grüebler, Greifensee (CH); Klaus Dorawa, Kiel (DE)

(73) Assignee: Alcon Inc., Fribourg (CH)

( * ) Notice: Subject to any disclaimer, the term of this patent is extended or adjusted under 35 U.S.C. 154(b) by 459 days.

(21) Appl. No.: 17/938,366

(22) Filed: Oct. 6, 2022

(65) Prior Publication Data

US 2023/0135924 A1 May 4, 2023

Related U.S. Application Data

(60) Provisional application No. 63/263,166, filed on Oct. 28, 2021.

(51) Int. Cl.
*A61F 9/007* (2006.01)
*A61B 17/34* (2006.01)

(52) U.S. Cl.
CPC ...... *A61F 9/00736* (2013.01); *A61B 17/3421* (2013.01); *A61B 17/3496* (2013.01)

(58) Field of Classification Search
CPC ............. A61F 9/00736; A61B 17/3421; A61B 17/3496
USPC ................... 604/157, 184; 606/184; 600/576
See application file for complete search history.

(56) References Cited

U.S. PATENT DOCUMENTS 3,805,787 A 4/1974 Banko
4,030,567 A 6/1977 Kondo
5,019,035 A 5/1991 Missirlian
5,190,050 A 3/1993 Nitzsche
5,217,465 A 6/1993 Steppe
5,312,354 A * 5/1994 Allen ................. A61B 17/3496 604/164.12
5,370,658 A 12/1994 Scheller
5,396,880 A 3/1995 Kagan et al.
5,779,680 A * 7/1998 Yoon .................. A61B 17/3417 604/164.12
6,312,402 B1 11/2001 Hansmann
6,575,989 B1 6/2003 Scheller
6,743,166 B2 * 6/2004 Berci ................ A61M 16/0488 600/130
6,749,601 B2 6/2004 Chin
6,908,476 B2 6/2005 Jud
6,945,984 B2 9/2005 Arumi
(Continued)

FOREIGN PATENT DOCUMENTS

CN 202426711 U 9/2012
CN 207755450 U 8/2018
(Continued)

*Primary Examiner* — Andrew Restaino
(74) *Attorney, Agent, or Firm* — Patterson + Sheridan, LLP

(57) ABSTRACT

A surgical tool for eye surgery that utilizes a stiffening sleeve and employs a needle of extendible reach. The reach off the needle into the eye is dynamically adjustable by forcible interaction between the stiffening sleeve and a cannula at an outer location of a patient's eye. An end of the tool may retract to facilitate extension of the needle for added reach. Additionally, the sleeve may be further independently retracted for even greater reach of the needle implement toward a surgical site within the eye of the patient.

11 Claims, 6 Drawing Sheets

(56) References Cited

U.S. PATENT DOCUMENTS

| | | | | |
|---|---|---|---|---|
| 7,207,980 | B2 | 4/2007 | Christian | |
| 7,338,494 | B2 | 3/2008 | Ryan | |
| 7,909,816 | B2 | 3/2011 | Buzawa | |
| 8,038,692 | B2 | 10/2011 | Valencia | |
| 8,187,293 | B2 | 5/2012 | Kirchhevel | |
| 8,202,277 | B2 | 6/2012 | Ryan | |
| 8,308,737 | B2 | 11/2012 | Ryan | |
| 8,845,666 | B2 | 9/2014 | Underwood | |
| 8,894,636 | B2 | 11/2014 | Gille et al. | |
| 9,060,841 | B2 | 6/2015 | Mccawley | |
| 9,138,346 | B2 | 9/2015 | Scheller | |
| 9,370,447 | B2 | 6/2016 | Mansour | |
| 9,585,788 | B2 | 3/2017 | Underwood | |
| 9,757,274 | B2 | 9/2017 | Scheller et al. | |
| 9,775,943 | B2 | 10/2017 | Scheller | |
| 9,795,505 | B2 | 10/2017 | Yu et al. | |
| 9,925,326 | B2 | 3/2018 | Scheller | |
| 9,931,244 | B2 | 4/2018 | Ryan | |
| 9,949,876 | B2 | 4/2018 | Mansour | |
| 10,045,883 | B2 | 8/2018 | Egli | |
| 10,085,883 | B2 | 10/2018 | Auld | |
| 10,179,007 | B2 | 1/2019 | Peterson | |
| 10,285,583 | B2 | 5/2019 | Parto | |
| 10,376,315 | B2 | 8/2019 | Scheller et al. | |
| 10,391,232 | B2 | 8/2019 | Scheller et al. | |
| 10,413,445 | B2 | 9/2019 | Scheller et al. | |
| 10,413,446 | B2 | 9/2019 | Bouch et al. | |
| 10,617,560 | B2 | 4/2020 | Ryan | |
| 10,639,197 | B2 | 5/2020 | Lopez | |
| 10,675,181 | B2 | 6/2020 | Murakami | |
| 10,828,192 | B2 | 11/2020 | Scheller et al. | |
| 10,898,373 | B2 | 1/2021 | Ryan | |
| 10,945,882 | B2 | 3/2021 | Ryan | |
| 11,020,270 | B1 | 6/2021 | Peyman | |
| 11,278,449 | B2 | 3/2022 | Ryan | |
| 2003/0195539 | A1 | 10/2003 | Attinger | |
| 2005/0033309 | A1 | 2/2005 | Ryan | |
| 2005/0209618 | A1 | 9/2005 | Auld | |
| 2007/0099149 | A1 | 5/2007 | Levy et al. | |
| 2007/0106300 | A1 | 5/2007 | Auld | |
| 2007/0255196 | A1 | 11/2007 | Wuchinich | |
| 2008/0195135 | A1 | 8/2008 | Attinger | |
| 2008/0255526 | A1 | 10/2008 | Bosse et al. | |
| 2009/0093800 | A1 | 4/2009 | Auld | |
| 2009/0131870 | A1 | 5/2009 | Fiser | |
| 2010/0063359 | A1 | 3/2010 | Okoniewski | |
| 2010/0228226 | A1 | 9/2010 | Nielsen | |
| 2012/0116361 | A1 | 5/2012 | Hanlon et al. | |
| 2013/0090531 | A1 | 4/2013 | Ryan | |
| 2013/0090635 | A1 | 4/2013 | Mansour | |
| 2013/0197488 | A1 | 8/2013 | Scheller et al. | |
| 2013/0281817 | A1 | 10/2013 | Schaller | |
| 2014/0121469 | A1 | 5/2014 | Meckel et al. | |
| 2014/0128896 | A1 | 5/2014 | Ryan | |
| 2014/0257200 | A1* | 9/2014 | Auerbach | A61B 17/3496 604/263 |
| 2015/0231687 | A1 | 8/2015 | Ookubo et al. | |
| 2016/0022256 | A1* | 1/2016 | Peterson | A61F 9/007 600/204 |
| 2017/0215855 | A1 | 8/2017 | Nunan | |
| 2017/0333251 | A1 | 11/2017 | Scheller et al. | |
| 2018/0104101 | A1* | 4/2018 | Lopez | A61F 9/00763 |
| 2018/0214307 | A1 | 8/2018 | Ryan | |
| 2018/0228651 | A1 | 8/2018 | Mansour | |
| 2018/0250164 | A1 | 9/2018 | Ryan | |
| 2018/0360660 | A1 | 12/2018 | Lopez | |
| 2019/0059936 | A1 | 2/2019 | Ryan | |
| 2019/0269556 | A1 | 9/2019 | Meckel | |
| 2019/0282322 | A1 | 9/2019 | Mirsepassi | |
| 2020/0163717 | A1 | 5/2020 | Hartkopf-ceylan | |
| 2020/0197217 | A1 | 6/2020 | Ryan | |
| 2021/0177652 | A1 | 6/2021 | Chen et al. | |
| 2021/0177653 | A1 | 6/2021 | Hallen | |
| 2021/0244567 | A1 | 8/2021 | Ryan | |
| 2021/0251805 | A1 | 8/2021 | Ryan | |
| 2021/0290438 | A1 | 9/2021 | Hallen | |
| 2022/0031509 | A1 | 2/2022 | Tazawa | |
| 2022/0192706 | A1 | 6/2022 | Grueebler et al. | |

FOREIGN PATENT DOCUMENTS

| | | | |
|---|---|---|---|
| DE | 651436 | C | 10/1937 |
| EP | 1782781 | A1 | 5/2007 |
| EP | 1955684 | A1 | 8/2008 |
| EP | 2760400 | B1 | 1/2018 |
| EP | 3191161 | B1 | 1/2020 |
| EP | 3656332 | A1 | 5/2020 |
| EP | 3352682 | B1 | 7/2020 |
| EP | 3332756 | B1 | 8/2020 |
| GB | 1448129 | A | 9/1976 |
| JP | 2009072221 | A | 4/2009 |
| JP | 2022040303 | A | 3/2022 |
| WO | 0119255 | A1 | 3/2001 |
| WO | 2010064670 | A1 | 6/2010 |
| WO | 2013133712 | A1 | 9/2013 |
| WO | 2017005795 | A1 | 1/2017 |
| WO | 2017053832 | A1 | 3/2017 |
| WO | 2017075514 | A1 | 5/2017 |
| WO | 2020059773 | A1 | 3/2020 |
| WO | 2021116932 | A1 | 6/2021 |
| WO | 2022130209 | A1 | 6/2022 |

* cited by examiner

EXTENDIBLE IMPLEMENT FROM WITHIN A STIFFENING SLEEVE AND TOOL BODY END

PRIORITY CLAIM

This application claims the benefit of priority of U.S. Provisional Patent Application Ser. No. 63/263,166 titled "EXTENDIBLE IMPLEMENT FROM WITHIN A STIFFENING SLEEVE AND TOOL BODY END," filed on Oct. 28, 2021, whose inventors are Reto Grüebler and Klaus Dorawa, which is hereby incorporated by reference in its entirety as though fully and completely set forth herein.

BACKGROUND

Over the years, many dramatic advancements in the field of minimally invasive surgical procedures have taken place. Accordingly, natural patient injury and healing times have been dramatically reduced. In the area of eye surgery as an example, previously inaccessible, injured or deteriorating tissue may be repaired or directly serviced through minimally invasive procedures. For example, regardless of the particular procedure, it is common that a vitrectomy will be included in at least part of the procedure. Vitrectomy is the removal of some or all of the vitreous humor from a patient's eye. In some cases, where the surgery was limited to removal of clouded vitreous humor, the vitrectomy may constitute the majority of the procedure. However, a vitrectomy may accompany cataract surgery, surgery to repair a retina, to address a macular pucker or a host of other issues.

In keeping with the example of eye surgery and a vitrectomy, the vitreous humor itself is a clear fibrous gel that may be removed by an elongated needle when inserted through a pre-placed cannula at the eye. More specifically, a vitrectomy probe is a surgical tool that is held by a surgeon at a gripping location with a needle emerging from the tool as described. The needle includes a central channel for removal of the vitreous humor. Further, the cannula provides a structurally supportive conduit strategically located at an offset location at the front of the eye, such as the pars plana. In this way, the probe needle may be guidingly inserted into the eye in a manner that avoids damage to the patient's lens or cornea.

The needle is generally guided and supported by a cannula and trocar assembly which has been prepositioned at the location of an incision through the pars plana as indicated. Thus, the needle may be securely advanced through to the interior of the eye to perform the surgical procedure. Of course, just as with a probe needle for a vitrectomy, a variety of other surgical implements may be similarly advanced through a cannula and trocar assembly for a variety of different surgical purposes. These may include forceps, scissors, light probe instruments and other instrumentation such as a scraper, backflush tool, or diathermy probe.

Over the years, minimally invasive surgeries, such as the described vitrectomies, have employed smaller and smaller implements for increasingly precise surgical maneuvers. For example, vitrectomy probe needles that traditionally may have been about 23 gauge may be about 25 or 27 gauge. This translates to reducing a needle diameter from just under about 0.5 mm (millimeters) to less than about 0.4 mm. Considering that a vitrectomy probe needle is likely to be of a few millimeters in length and hollow, this increasingly thin gauge implement is likely to be quite flexible. For other instruments, a similar flexibility issue emerges as the implement size becomes increasingly smaller, including for a vitrectomy probe cutter needle.

Increased pliability or flexibility for a surgical implement is not necessarily helpful to a surgeon during a procedure. Generally speaking, the surgeon is better aided by a degree of rigidity in the implement that affords a greater degree of control. That is, manual manipulation of the implement by the surgeon at an exterior location is more likely to reliably transfer to the surgical site if the implement is more inflexible. So, for example, in the case of a vitrectomy procedure, the probe may include a grip from which the needle extends toward and through the noted cannula structure at the eye. A larger and more rigid stiffening sleeve may extend from the structural support of the cannula and back toward the body and grip of the tool. Thus, at least in the space between the surgeon's grip location and the front of the eye, bending of the needle may be avoided/reduced due to the presence of the stiffening sleeve. Rather, a secure and reliably linear translation of movement from the grip to a pivot location at the surface of the eye is displayed (e.g. where the stiffening sleeve contacts the cannula). Once more, the actual length of the needle which presents within the eye and is not structurally bound by the stiffening sleeve is limited. Thus, bending of the needle is further minimized.

Unfortunately, utilizing a stiffening sleeve as detailed, places a notable surgical limitation on such a procedure. Specifically, a dimensional limitation is presented by the use of a sleeve. For example, where a 1 cm (centimeter) sleeve is utilized on a 3 cm needle, effectively 2 cm of working needle length is utilized for the procedure within the patient's eye. That is, in sandwiching the sleeve between the cannula and the grip location, securely maintaining the sleeve means that the needle is positioned right at 2 cm of depth into the patient's eye. Forcing the cannula deeper is not really possible without forcing injury to the eye at the cannula location. Once more, removing the needle to a shallower depth relaxes the stability of the sleeve, thus losing much of its supportive benefit.

Of course, where the targeted surgical location is greater than 2 cm from the cannula and eye surface, this means that utilizing the noted sleeve will prevent the necessary surgical access. By the same token, the target location may be well under 2 cm which could result in overshooting by the needle and eye injury to the patient. The targeted surgical location may also span a range of depths within the eye during the same procedure.

SUMMARY

A surgical tool is provided. The tool includes a body with an end that is manually secured by a surgeon for a surgical procedure. An implement of the tool extends from within the end to facilitate the procedure. A stiffening sleeve is provided about the implement for stabilization of the implement during the procedure. A biasing mechanism is coupled to the end of the tool body which allows for its retractability for guided extension of the implement in response to the stiffening sleeve contacting a cannula structure at a location adjacent the surgical procedure site. The biasing mechanism may be additionally coupled to the stiffening sleeve to guidably facilitate its retraction for still further extension of the implement.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Figure 1:
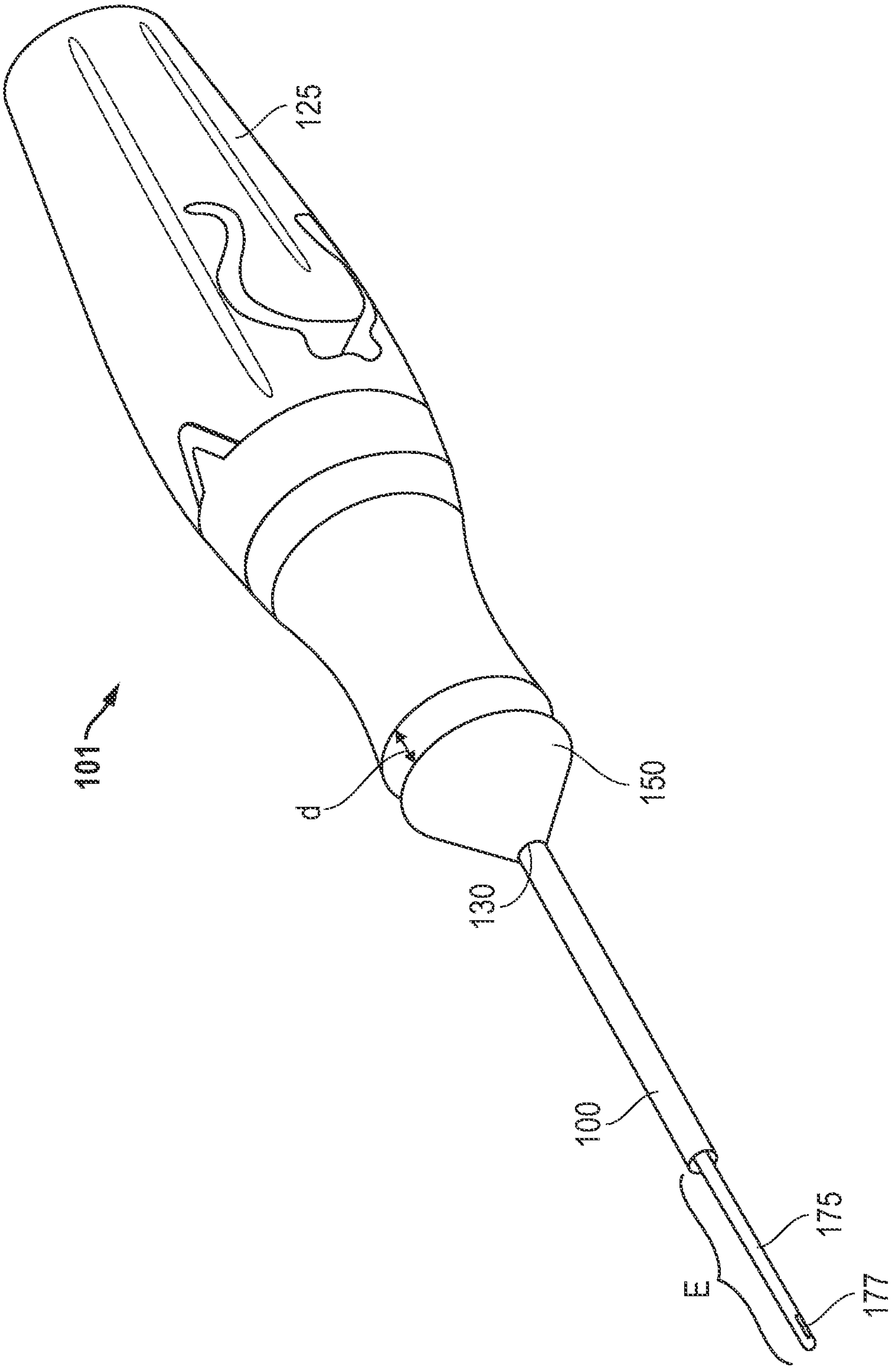
FIG. 1 is a side perspective view of a surgical tool employing a needle aided by an embodiment of a dynamically extendable implement.

Embodiments are described with reference to certain types of surgical procedures. In particular, an overview of a vitrectomy probe is illustrated in FIG. 1. For example, vitreous humor removal, perhaps to address a vitreous hemorrhage, may be noted with reference to FIGS. 5A and 5B. Of course, a forceps tool, scissors or any number of other optical surgical devices may employ extendible implement embodiments as detailed herein. These may include light probe instruments and other instrumentation such as a scraper, backflush tool, or diathermy probe. Further, while a vitrectomy procedure is largely discussed herein, embodiments of a vitrectomy probe as detailed herein may be utilized to address retinal detachments, macular pucker, macular holes, vitreous floaters, diabetic retinopathy or a variety of other eye conditions. Additionally, while vitrectomy and other eye surgeries often benefit from the use of fairly thin implements, other types of surgeries may benefit from the unique architecture and techniques detailed herein. Indeed, so long as a supportive stiffening sleeve is employed in combination with an implement or needle of extendible reach, appreciable benefit may be realized.

Figure 5A:
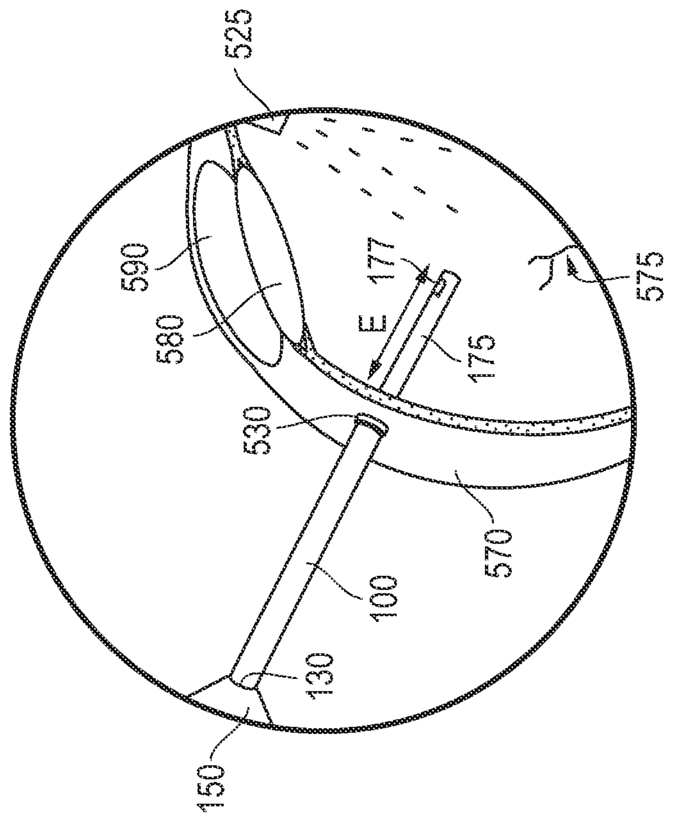
FIG. 5A is an overview illustration of a surgical procedure performed with the tool of FIG. 1 with the implement in an initial position.
Figure 5B:
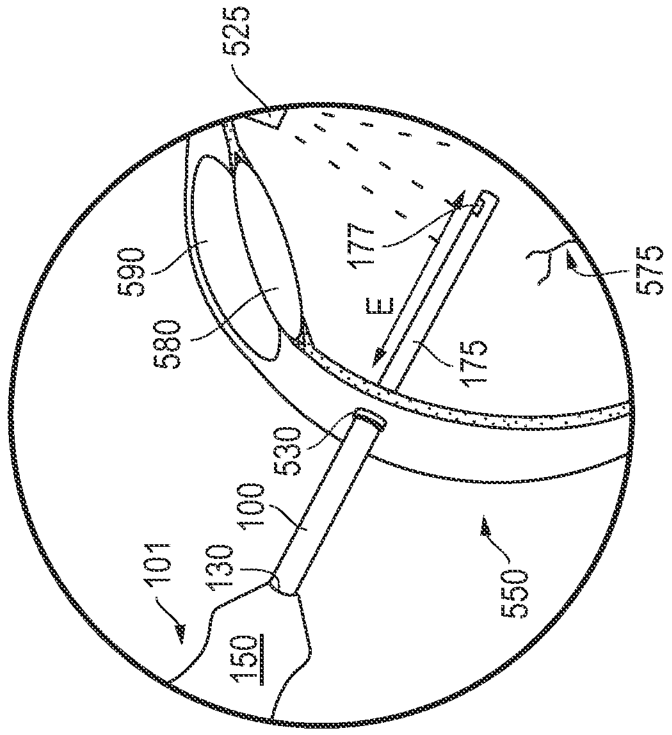
FIG. 5B is an overview illustration of the surgical procedure of FIG. 5A with the implement fully extended.

Referring now to FIG. 1, a side perspective view of a surgical tool 101 is shown employing an implement 175 in the form of a needle. As detailed herein, a surgical procedure performed with the tool 101 may be aided by the fact that the implement 175 is dynamically extendable. Specifically, the tool 101 for the embodiment shown, is a vitrectomy probe with a stiffening sleeve 100. This sleeve 100 is configured to provide a supportive structure about the relatively thin implement 175 up to the point of contacting a cannula structure 530 as illustrated in FIGS. 5A and 5B. Upon making such contact, the degree to which the implement 175 extends from within the sleeve 100 may be dynamically adjusted through various techniques detailed herein (note the extension (E)). In one embodiment, this may be achieved by the retraction of a tool body end 150 in general unison with the sleeve 100, toward a proximal end or shell 125. In this manner, a distance (d) is closed and the implement 175 is further extended as is detailed below. Indeed, with respect to the embodiment of FIGS. 1, 2A and 2B, this generally unitary retraction of the end 150 and sleeve 100 together is the manner by which the increase in the extension (E) is attained. However, as is detailed further below, separate further retraction of the sleeve 100, into an end orifice 130, even after the closure of (d), for further increasing the extension (E) is additionally possible.

Continuing now with specific reference to FIG. 1, the needle or implement 175 is considered dynamically adjustable with respect to the degree of extension (E) due to the retractability of the tool end 160 as noted above as well as the stiffening sleeve 100 as detailed further below. In the embodiment shown, the tool 101 is a vitrectomy probe which may be utilized in a procedure as is also detailed further herein. However, other types of instruments for a variety of different surgical applications may take advantage of such dynamic adjustability.

The implement 175 may be relatively thin. In particular, it is not uncommon for a 25-35 mm long needle implement 175 to be higher than 25 gauge sizing. Thus, even where stainless steel or other suitably durable surgical materials are employed, the needle 175 alone may lack a desired rigidity from the surgeon's perspective and be prone to a degree of bending.

The noted lack of rigidity displayed by the needle 175 may be addressed by the inclusion of the illustrated sleeve 100 about the needle 175. The illustrated sleeve 100 may extend from the tool 101 at its gripping element or end 150 a predetermined distance with a certain amount of needle extension (E). However, this may be intentionally adjusted by the surgeon over the course of a procedure. That is, the surgeon may advantageously exert control over how much sleeve support is provided versus how much reach or extension (E) may be attained by the needle implement 175. This may take place in a dynamic fashion with the reach of the implement 175 changing throughout the course of a given surgical procedure.

Continuing with reference to FIG. 1, the tool 101 includes a proximal portion, rearward of the tool body end 150, that may be referred to herein as a shell 125. The shell 125 may be used as a form of ergonomic support or, in one embodiment, the shell 125 may be removable, depending on surgeon preference. For example, in the case of a vitrectomy probe, the surgeon may hold the instrument at the end 150, between a thumb and index finger, with the shell 125 resting at the perlicue of the hand and protectively encasing instrument components therein. The implement 175 may support a cutter therein which interacts with a port 177 thereof for the controlled uptake of vitreous humor as described further below. For such a procedure, it is the dynamic extendability (E) of the implement 175 from within the sleeve 100 and end 150 that uniquely supports and facilitates the surgeon's efforts in this endeavor.

Figure 2A:
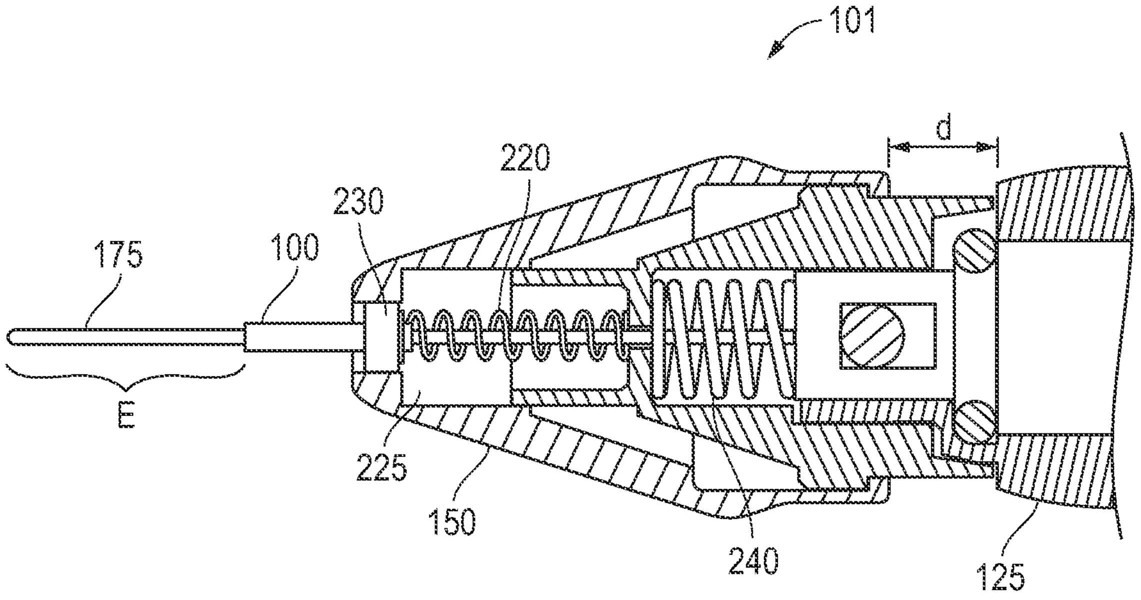
FIG. 2A is a side cross-sectional view of an end of the surgical tool of FIG. 1 highlighting an internal biasing mechanism.

Referring now to FIG. 2A, a side cross-sectional view of an end 150 of the surgical tool 101 of FIG. 1 is shown highlighting an internal biasing mechanism 220. In the embodiment illustrated, the mechanism 220 is a spring anchored within a biasing chamber 225 to act against a base 230 of the sleeve 100 within the tool end 150. With the base 230 secured to the tool end, force applied to the base 230 by the sleeve 100 may act to shift the position of the end 150 and close the distance (d). Indeed, with added reference to FIG. 2B, this has occurred with the end 150 meeting the shell 125 as noted at 200. With the sleeve 100 and the end 150 shifting as indicated, there may be a corresponding increase in the extension (e.g. from (E) of FIG. 2A to (E') of FIG. 2B).

Increasing the extension by an amount equal to the eliminated distance (d) (i.e. to E') may be a matter of surgical preference as the distal end of the sleeve 100 interacts with a cannula structure 530 as detailed below with respect to FIGS. 5A and 5B. Thus, the surgeon is able to dynamically extend the length of the needle implement 175 by perhaps a few millimeters in a steady manner as guided by the resisting biasing mechanism 220. Thus, a controlled manner of extending the reach of the instrument for a surgical procedure may be available.

Figure 2B:
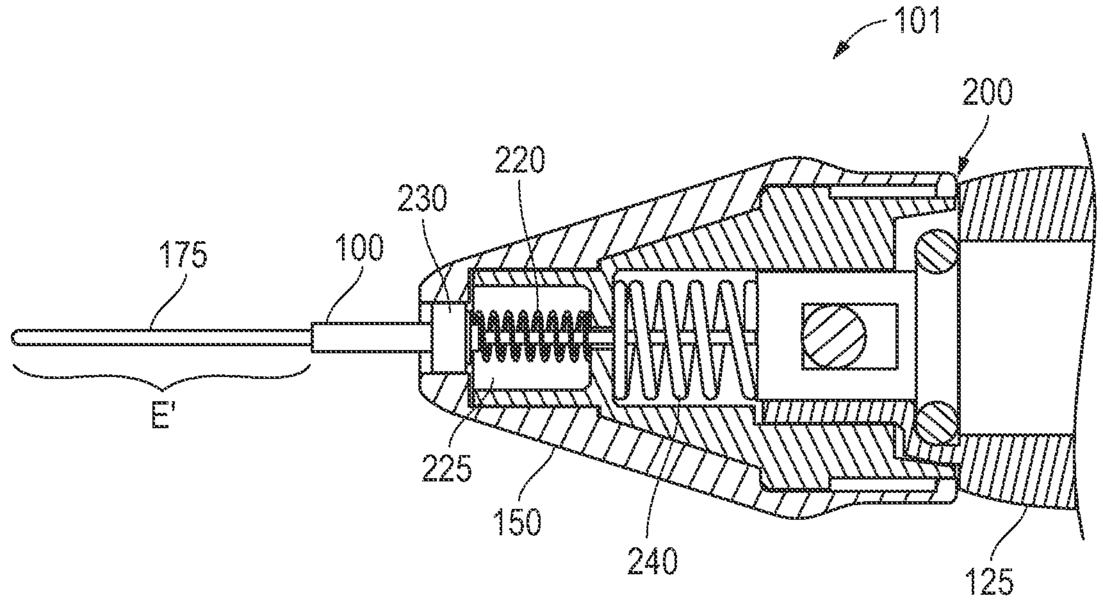
FIG. 2B is a side cross-sectional view of the tool end of FIG. 2A with the end responsively shifted to extend the implement.

Note that another internal spring 240 and other components of the tool 101 are illustrated in FIGS. 2A and 2B. These may be employed for other purposes, such as actuating forceps or scissors where other types of implements are utilized. However, in other embodiments detailed below, such internal components may be utilized to aid in even further extension of the implement 175.

Figure 3:
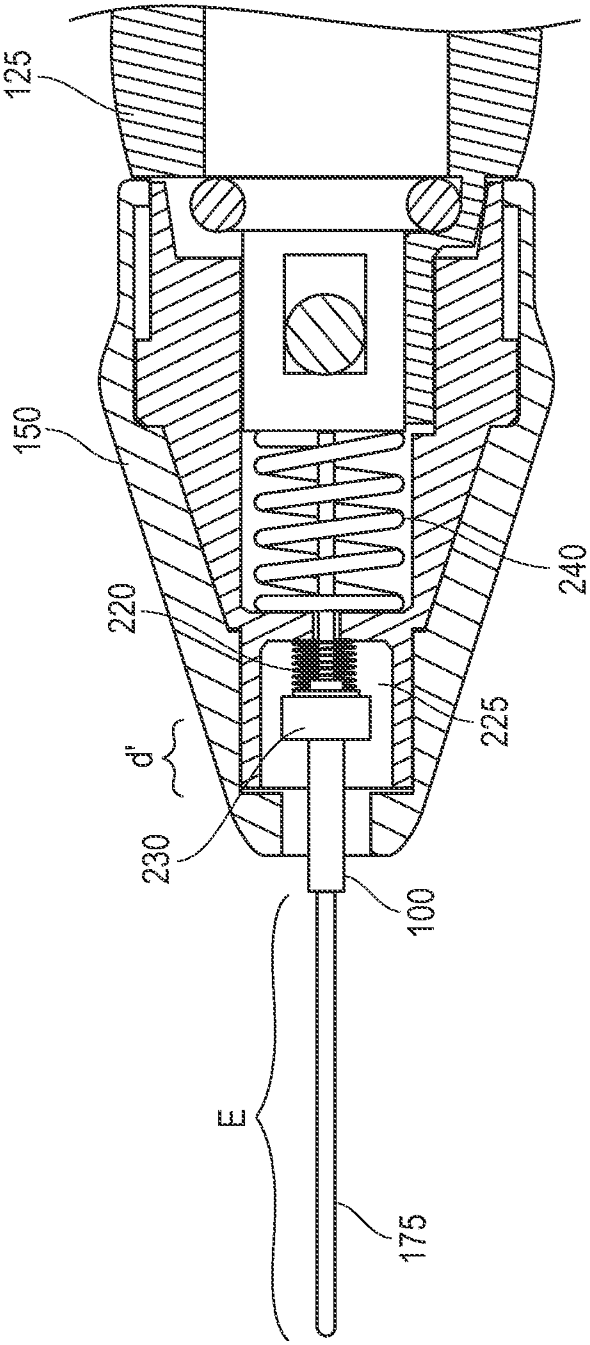
FIG. 3 is a side cross-sectional view of the tool end of FIG. 2B with the implement further extended by a shift in position of a stiffening sleeve of the tool.

Referring now to FIG. 3, a side cross-sectional view of the tool end 150 of FIG. 2B is illustrated in an embodiment where the implement 175 may be further extended (e.g. to (E")). For example, in this embodiment, even after the shift in position of the end 150 to meet the shell 125 as described above, the base 230 may be shifted by an additional distance (d") to attain the added extension (E"). For example, in one embodiment, added force applied by the surgeon may be used to attain shearing of the base 230 from the tool end 150 to allow for additional compression of the biasing mechanism (spring 220). So, for example, with added reference to FIGS. 5A and 5B, once a predetermined force is applied by the surgeon, directed at the contact point of the sleeve 100 and cannula 530, the shearing and additional shifting of the sleeve 100 apart from the end 150 may be attained. In this manner added reach of the implement 175 into a patient's eye 550 may be achieved (e.g. to the added extension (E") shown). Alternatively, different internal architecture may be employed as detailed below to attain the added extension (E") without requirement any requirement of shearing (see FIGS. 4A and 4B discussed below).

Figure 4A:
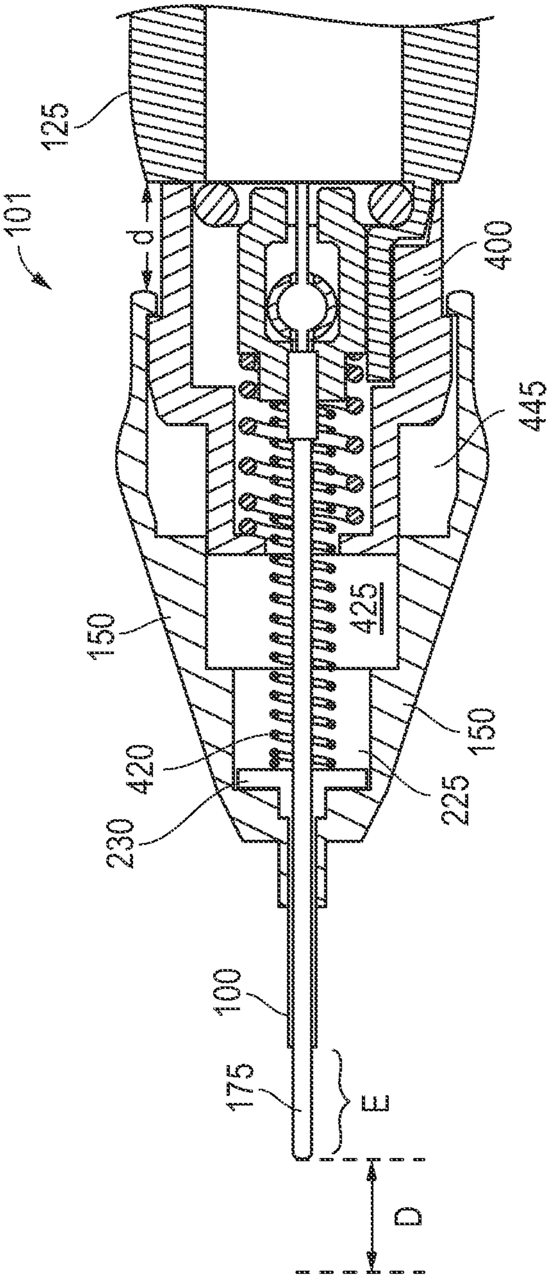
FIG. 4A is a side cross-sectional view of the tool end of FIG. 1 employing an alternate embodiment of internal biasing mechanism.

Referring now to FIG. 4A, a side cross-sectional view of the tool end 150 of FIG. 1 is illustrated for which an alternate embodiment of internal biasing mechanism is utilized. In this case, rather than employing a single spring 220 within a biasing chamber 225, as illustrated in FIGS. 2A and 2B, another proximal chamber 425 of differing architecture is also employed. In this way, successive shifting or closures of different chambers 225, 425 may be utilized to achieve the full extension (E") of FIG. 4B. As detailed below, utilizing discrete chambers 225, 425 for successive shifting and extension of the implement 175 means that shearing for sake of movement of the base 230 to achieve the full extension (E") may be avoided.

Figure 4B:
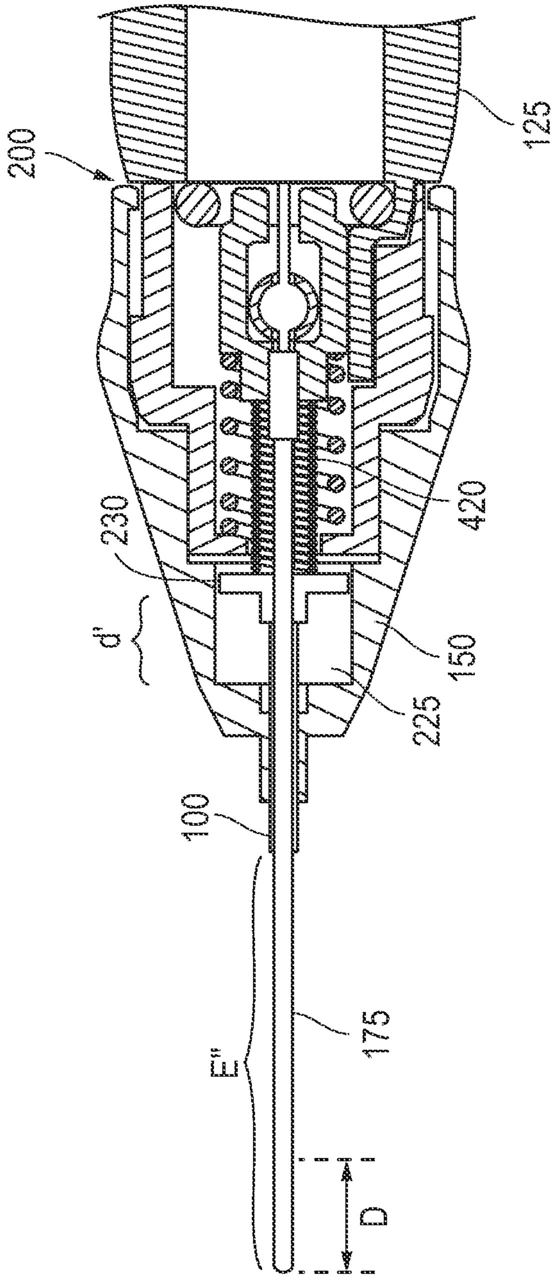
FIG. 4B is a side cross-sectional view of the tool end of FIG. 4A with the biasing mechanism fully collapsed for full extension of the implement.

Continuing with reference to FIG. 4A, the end of the sleeve 100 is again configured to contact a cannula 530 as illustrated in FIGS. 5A and 5B, as a manner of initiating a shift of the tool end 150 in order to close the distance (d). This is again visible with respect to the contact between the end 150 and the shell 125 as shown in FIG. 4B (see contact point 200). In order to attain this shifting of the tool end 150, the proximal chamber 425 is closed. Note that some level of resistance to this closure is provided for overall stability of the tool 101. For example, there may be little to no clearance between the end 150 and underlying housing 400 of the tool 101. Indeed, in one embodiment, a predetermined degree of frictional resistance between these features 150, 400 may be provided or even air pressure, another spring or other suitable resistance located within the proximal chamber 425. So long as the resistance is of a lesser force than the spring 420 that runs through the biasing chamber 420, the proximal chamber 425 will close in advance of shifting of the base 230 and further implement extension described below. Thus, for the embodiment illustrated, extension of the implement 175 may begin in sequence with shifting of the end 150 to close the proximal chamber 425 and the distance (d).

Referring now to FIG. 4B, the biasing mechanism spring 420 that runs through both chambers 225, 425 is now shown compressed, with the base 230 having subsequently shifted after the closure of the proximal chamber 425 and initial distance (d) of FIG. 4A. That is, another distance (d') has now also been closed to further extend the implement to the extension position illustrated (E"). Indeed, the amount of additional reach now provided to the implement 175 is a distance (D) that is roughly equal to the initial end closure distance (d) plus the subsequent distance (d') of the shifting of the base 230. That is, with added reference to FIGS. 5A and 5B, once the sleeve 100 is in contact with the cannula 530, an initial shift of the end 150 may be controllably exerted by the surgeon to attain an initial extended reach of the implement 175 into the eye 550 for a procedure (e.g. as the end 150 closes the proximal chamber 425 and distance (d)). This reach may be further extended by the surgeon through application of some degree of added force (e.g. as the base 230 travels over the distance (d')).

It is worth noting that there is no particular requirement that the sequence of shifting occur as indicated above. For example, in another embodiment, the travel of the base 230 may face a lesser degree of resistance and occur as the initial manner of extending the implement 175. In this embodiment, closure of the proximal chamber 425 and the distance (d) of FIG. 4A may occur after the travel of the base 230 as described. Furthermore, these movements may occur in relative unison with neither being particularly more or less resistant to the extension of the implement 175 than the other. Regardless, so long as both end 150 and internal base 230 travel movements are cumulatively attainable, the surgeon is afforded an added degree of reach for the implement 175 that may be beneficial to the surgery as described below.

Referring directly now to FIGS. 5A and 5B, an overview illustration of a surgical procedure performed with the tool 101 of FIG. 1 is shown. More specifically, the reach of the tool implement 175 into a patient's eye 550 is extended from an initial position (E) to a fully extended position (E") in a multifaceted manner. For embodiments herein this includes the shifting of a tool end 150 in a proximal direction in unison with a sleeve 100 over the implement 175. Further, the sleeve 100 may be supplementally shifted proximally within the end 150 for added reach of the implement 175.

Continuing with reference to FIGS. 5A and 5B, a side cross-sectional overview of a patient's eye 550 is shown wherein the procedure is a vitrectomy procedure. During the procedure, the implement 175 of the tool 101 is inserted through a preplaced cannula 530 and directed toward a region 510 where vitreous humor is to be removed. A suction is applied and the port 177 is used for the uptake of the vitreous humor or other substances. For example, in the procedure illustrated, a hemorrhage may be taking place in the region 510 such that blood is drawn into the port 177 along with the vitreous humor.

Notice that while the needle 175 reaches into the interior of the eye 550 for the procedure as described, the stiffening sleeve 100 which surrounds the needle 175 does not. Rather, the end of the sleeve 100 is securely rested at the internal structure of the cannula 530. More specifically, the interior cannula structure may be of a funnel shaped or other accommodating morphology so as to receive and support the end of the stiffening sleeve 100 during the procedure. By the same token, the center of the cannula 530 includes an orifice of sufficient size to allow passage of the needle 175 therethrough. Of course, the orifice would also be too small to allow the same passage of the sleeve 100. So, for example, in one embodiment, the orifice may be about 0.475 mm in diameter so as to allow for passage of a 26 gauge and smaller needle 175 (e.g. 0.46 mm diameter or smaller). At the same time, this orifice would also prevent passage of a 25 gauge and larger sleeve 100 (e.g. 0.515 mm diameter or larger). Of course, a variety of different dimensional combinations may be employed so as to promote needle implement passage and prohibit sleeve passage through an orifice of the cannula 530 as described.

With the sleeve 100 stably interfacing the interior structure of the cannula 530, the surgeon may steer the needle about a pivot point at the cannula 530. In this manner a certain stabilized working area is attained with the needle 175 at the interior of the eye 550. Further, between the cannula 530 and the tool 101 of FIG. 1, where unintended bending might otherwise be of concern, supplemental stiffness is provided by the sleeve 100.

As alluded to above, for the example of a vitrectomy procedure, a cutter is reciprocating within the needle implement 175 during this delicate procedure. The surgery illustrated also includes a light instrument 525 reaching into the eye 550 through another cannula. In both circumstances, the cannulas 530 are positioned in an offset manner at the sclera 570. In this way, the more delicate cornea 590 and lens 580 may be avoided.

By the same token, the optic nerve and retina, located out of view at the back of the eye 550, are also quite delicate. With this in mind, the stiffening sleeve 100 may play an initial role in preventing the needle implement 175 from unintentionally reaching too far into the eye 550. By the same token, however, the surgeon may exert an intentional force such that the implement 175 guidingly and controllably achieves an extended reach (E") as illustrated here according to the techniques detailed above.

Figure 6:
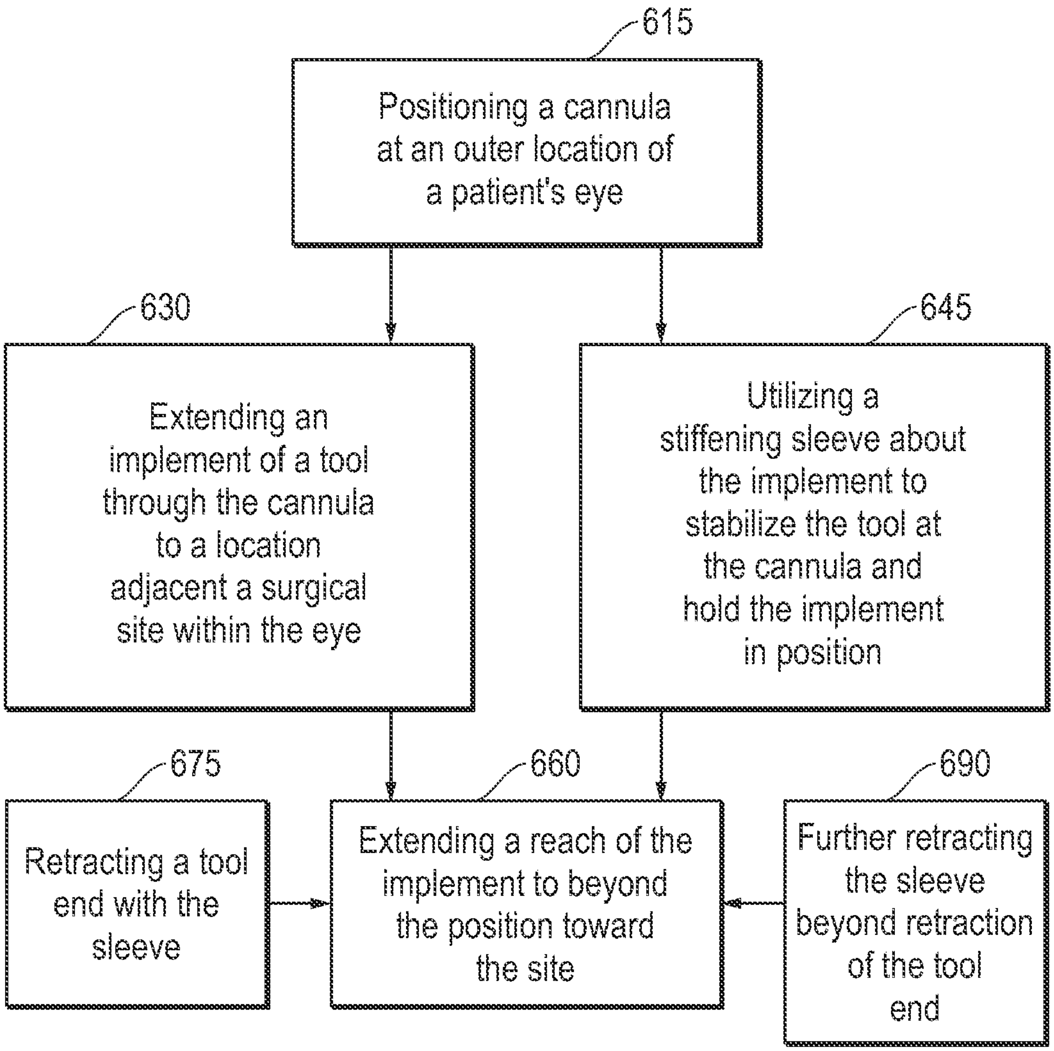
FIG. 6 is a flow-chart summarizing an embodiment of performing a minimally invasive surgical procedure with an implement aided by a dynamic extension.

Referring now to FIG. 6, a flow-chart summarizing an embodiment of performing a minimally invasive surgical procedure with an implement having dynamic extendible reach is illustrated. As indicated at 615, a cannula is positioned at an outer location of a patient's eye to provide supportive structure for a surgical procedure. An implement such as a needle of a surgical tool may be guided through an orifice of the cannula as noted at 630. Thus, the needle may extend from the surgical tool and beyond the cannula toward a surgical site. However, as indicated at 645, a stiffening sleeve of the tool that is located about the needle may be used to stabilize the tool at the cannula and hold the implement needle in position.

With the above scenario in place for a surgical procedure, the reach of the implement may be extended further toward the surgical site from the initial sleeve supported position (see 660). Specifically, this may occur by way of a retraction of a tool end as indicated at 675 which also effects a commensurate sleeve retraction for sake of increasing implement reach. Furthermore, the sleeve may undergo an additional degree of retraction beyond the tool end retraction (see 690). As detailed hereinabove, these modes of retraction may occur independently or in sequence with the tool end retraction preceding the independent sleeve retraction (or vice versa). Further, these cumulative retractions may take place in a relatively simultaneous or overlapping manner. So long as multiple modes of retraction are available for cumulative enhancement of implement reach, appreciable benefit may be available to the surgeon for sake of the procedure.

Embodiments described hereinabove include architecture and techniques that allow for practical use of a stiffening sleeve to support a surgical procedure employing a relatively thin surgical implement. However, rather than remain reliant on the length of the stiffening sleeve to determine surgical access with the implement, multiple cumulative modes of extending reach of the implement toward an interior surgical site may be employed as indicated above.

The preceding description has been presented with reference to presently preferred embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

We claim:

1. A surgical tool comprising:

a tool body with an end configured to be manually secured by a user for a surgical procedure;

a surgical implement extending from the end of the tool body to attain surgical access to a tissue region of a patient for the surgical procedure;

a stiffening sleeve about the surgical implement for stabilizing the surgical implement during the surgical procedure at the tissue region, wherein the stiffening sleeve further comprises a stiffening sleeve base; and a biasing mechanism coupled to the end of the tool body configured to allow proximal retraction of both the end of the tool body and the stiffening sleeve in unison upon force directed against the biasing mechanism through the stiffening sleeve base, wherein upon retraction of the end of the tool body and the stiffening sleeve in unison, the biasing mechanism is further configured to allow the stiffening sleeve to further retract into an orifice at the end of the tool body to extend a reach of the surgical implement in response to the user contacting a cannula structure at a location adjacent the tissue region with the stiffening sleeve, wherein the further retraction of the stiffening sleeve occurs through shearing of the stiffening sleeve base from contact with the end of the tool body.

2. The surgical tool of claim 1 wherein the proximal retraction of the end of the tool body is toward a proximal portion of the surgical tool.

3. The surgical tool of claim 1 wherein the biasing mechanism is a spring housed within a chamber of the end of the tool body for support in guiding the proximal retraction of the end of the tool body.

4. The surgical tool of claim 3 wherein the chamber is a first chamber that reduces in size for the proximal retraction of the end of the tool body, the surgical tool further comprising a second chamber that reduces in size for the further retraction of the stiffening sleeve to further increase the reach of the surgical implement.

5. The surgical tool of claim 1 wherein the surgical implement is greater than about 25 gauge to support eye surgery and the surgical implement further supports one of a forceps, a scissors, a scraper, a backflush tool, a diathermy probe, an illumination probe, and a port for a vitrectomy procedure.

6. The surgical tool of claim 5 wherein the surgical tool is a vitrectomy probe and the surgical implement is a needle with a port opening to a cutter for uptake of vitreous humor from an eye of the patient.

7. The surgical tool of claim 1, wherein the surgical implement is configured to be inserted into an eye and the cannula structure is a trocar cannula configured for insertion into an eye.

8. The surgical tool of claim 1, wherein the biasing mechanism consists of a single spring.

9. A surgical system comprising:

a cannula for positioning at an outer surface of an eye; and a surgical tool with a surgical implement extending from a stiffening sleeve at an end of the surgical tool, the surgical implement having a given reach into the eye, the given reach extendable by a biasing mechanism in the surgical tool facilitating a retraction of the end of the surgical tool and the stiffening sleeve;

wherein the biasing mechanism is configured to allow proximal retraction of both the end of the surgical tool and the stiffening sleeve in unison upon force directed against the biasing mechanism through a stiffening sleeve base, wherein upon retraction of the end of the surgical tool and the stiffening sleeve in unison, the biasing mechanism is further configured to allow the stiffening sleeve to further retract into an orifice at the end of the surgical tool to extend the given reach of the surgical implement in response to a user contacting the cannula at a location adjacent the outer surface of the eye with the stiffening sleeve;

wherein the further retraction of the stiffening sleeve occurs through shearing of the stiffening sleeve base from contact with the end of the surgical tool.

10. The surgical system of claim 9 wherein the surgical system is used for one of a forceps application, a scissors application, a scraper application, a backflush tool application, a diathermy probe application and a vitrectomy procedure within the eye via the surgical implement.

11. The surgical system of claim 9, wherein the biasing mechanism consists of a single spring.

* * * * *